United States Patent [19]

Oxford et al.

[11] 4,140,713
[45] Feb. 20, 1979

[54] PHENYLETHANOLAMINE THERAPEUTIC AGENTS

[75] Inventors: Alexander W. Oxford, Royston; Ian H. Coates, Sandy, both of England

[73] Assignee: Allen & Hanburys Limited, London, England

[21] Appl. No.: 873,765

[22] Filed: Jan. 31, 1978

[30] Foreign Application Priority Data

Feb. 3, 1977 [GB] United Kingdom ................ 4419/77

[51] Int. Cl.² .................... C07C 91/06; C07C 143/78; C07C 143/80
[52] U.S. Cl. .......................... 260/556 AR; 260/556 B
[58] Field of Search ......... 260/556 AR, 556 B, 562 B

[56] References Cited

U.S. PATENT DOCUMENTS

| | | | |
|---|---|---|---|
| 3,860,647 | 1/1975 | Colella et al. ................ | 260/556 AR |
| 4,034,112 | 7/1977 | Smith ........................ | 260/556 AR X |

*Primary Examiner*—Allen B. Curtis
*Attorney, Agent, or Firm*—Bacon & Thomas

[57] ABSTRACT

Compounds of the general formula:

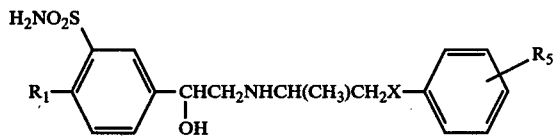

and non-toxic physiologically acceptable salts thereof, in which $R_1$ is a halogen atom or a group $NR_2R_3$;

$R_2$ and $R_3$, which may be the same or different, are hydrogen or ($C_1$–$C_6$) straight or branched chain alkyl or $R_2$ and $R_3$ may, together with the nitrogen atom, form a 5 or 6 membered heterocyclic ring which may contain a further hetero atom selected from O, N or S; or $R_2$ may be hydrogen and $R_3$ may by group $R_4CO$ or $R_4SO_2$ where $R_4$ is hydrogen or alkyl ($C_{1-4}$);

$R_5$ is hydrogen or one or more halogen atoms or hydroxy or alkoxy ($C_{1-4}$) groups; and X is $CH_2$, O or a group $NR_6$ where $R_6$ is hydrogen or alkyl ($C_{1-4}$). These compounds block $\beta$-adrenoreceptors.

15 Claims, No Drawings

PHENYLETHANOLAMINE THERAPEUTIC AGENTS

This invention relates to new benzenesulphonamide derivatives, to the preparation and use thereof, and to pharmaceutical compositions containing them.

We have found that certain benzene sulphonamide derivatives are useful for treating cardiovascular disorders such as angina and hypertension through their ability to block $\beta$-adrenoreceptors. A number of these compounds additionally have a useful blocking action on $\alpha$-adrenoreceptors; the combined $\alpha$- and $\beta$-blocking activities of such compounds make them particularly useful for the treatment of hypertension. They may also be useful in the treatment of peripheral vascular diseases e.g. Raynaud's disease and in the treatment of cardiac arrythmias.

According to the invention therefore, there are provided compounds of the general formula I:

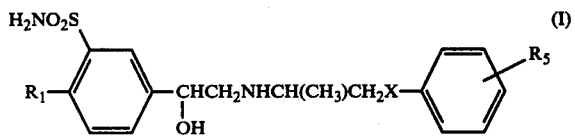

in which
R$_1$ is a halogen atom or a group NR$_2$R$_3$;
R$_2$ and R$_3$, which may be the same or different, are hydrogen or (C$_1$–C$_6$) straight or branched chain alkyl or R$_2$ and R$_3$ may, together with the nitrogen atom, form a 5 or 6 membered heterocyclic ring as, for example, a piperidine or pyrrolidine ring, which may contain a further hetero atom selected from O, N or S as, for example, piperazine; or R$_2$ may be hydrogen and R$_3$ may be group R$_4$CO or R$_4$SO$_2$ where R$_4$ is hydrogen or alkyl (C$_{1-4}$);
R$_5$ is hydrogen or one or more halogen atoms or hydroxy or alkoxy (C$_{1-4}$) groups; and
X is CH$_2$, O or a group NR$_6$ where R$_6$ is hydrogen or alkyl (C$_{1-4}$).

Preferred compounds according to the invention are those in which R$_1$ is chlorine, fluorine or an amino, alkyl (C$_{1-4}$) amino or dialkylamino group, particularly a dimethylamino group. R$_5$ is preferably hydrogen or halogen, in particular fluorine and where R$_5$ is halogen this may be in the para or meta position. X is preferably CH$_2$.

A particularly preferred group of compounds is made up of the following compounds. These compounds in particular demonstrate ability to block both $\alpha$- and $\beta$-adrenoreceptors.

2-Fluoro-5-[1-hydroxy-2-[[3-(4-fluorophenyl)-1-methylpropyl]-amino]ethyl]benzenesulphonamide.
2-Fluoro-5-[1-hydroxy-2[(1-methyl-3-phenylpropyl)amino]ethyl]benzenesulphonamide.
2-Dimeethylamino-5-[1-hydroxy-2-[(1-methyl-3-phenylpropyl)amino]ethyl]benzenesulphonamide.
2-Amino-5-[1-hydroxy-2-[(1-methyl-3-phenylpropyl)amino]ethyl]benzenesulphonamide.
5-[1-Hydroxy-2-[(1-methyl-3-phenylpropyl)amino]ethyl]-2-methylaminobenzenesulphonamide.
2-[Butylmethylamino)-5-[1-hydroxy-2-[(1-methyl-3-phenylpropyl) amino]ethyl]benzenesulphonamide.
2-Fluoro-5-[1-hydroxyl-2-[[3-(3-fluorophenyl)-1-methylpropyl]amino]ethyl]benzenesulphonamide.
2-(Ethylmethylamino)-5-[1-hydroxy-2-[(1-methyl-3-phenylpropyl) amino]ethyl]benzenesulphonamide.

The compounds of the invention include all possible diastereoisomers and optical enantiomorphs and mixtures thereof. The invention also includes non-toxic physiologically acceptable salts thereof, such as acid addition salts with inorganic or organic acids. Particular salts include hydrochlorides, maleates, tartrates etc.

The blocking actions on the $\alpha$- and $\beta$-adrenoreceptors were demonstrated in the bilaterally vagotomised anaesthetised dog. The compounds were administered by injection through a cannulated femoral vein.

The $\beta$-blocking activities of the compounds were determined from their ability to antagonise increases in heart rate induced by intravenous (-)isoprenaline; from the results obtained, DR$_{10}$ values were calculated for each antagonist. The DR$_{10}$ value is the dose of antagonist required to produce a 10-fold shift to the right of the agonist dose-response curve for increases in heart rate.

The $\alpha$-blocking activities of the compounds were determined from their ability to prevent increases in diastolic blood pressure induced by intravenous phenylephrine. The $\alpha$-blocking activity was quantified as a DR$_{10}$ value as described above.

The compounds according to the invention may be prepared by a number of processes.

In one process, the compounds of the invention may be prepared by reacting ketones of general formula (II)

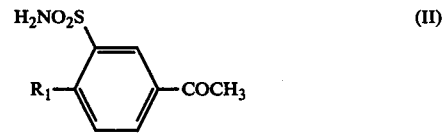

in which R$_1$ has the above stated meaning, with a halogen, preferably bromine, to form haloketones of formula (III)

followed by condensation with an amine NHR$_7$R$_8$, in which R$_7$ represents benzyl or the group R, where R is the group of formula (IV)

and R$_8$ represents hydrogen or benzyl, to give aminoketones of formula (V)

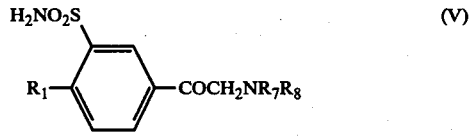

where R$_7$ and R$_8$ have the meanings given above.

The ketone group in a compound of formula (V) is then reduced to a CHOH group with a suitable reducing agent such as a complex metal hydride e.g. sodium borohydride to give a compound (VI)

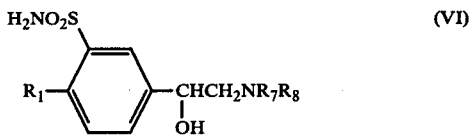

where $R_7$ and $R_8$ are as defined above. The compounds of formula (VI) in which $R_7$ is a group R and $R_8$ is hydrogen are compounds of the invention.

Alternatively, the reduction may be carried out by catalytic hydrogenation in the presence of a noble metal catalyst for example platinum or palladium or mixtures thereof, to give 1-phenyl-2-aminoethanol derivatives of formula (VII)

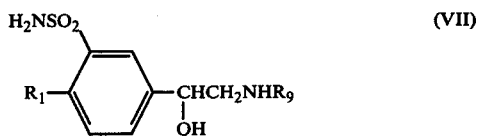

where $R_9$ represents hydrogen or the group R. The compounds of formula (VII) in which $R_9$ represents the radical R are compounds of the invention.

When a non-catalytic reduction procedure is used to reduce the aminoketone (V), benzyl groups in the molecule are not affected. In order to convert such benzyl groups into hydrogen atoms, a subsequent catalytic hydrogenolysis may be effected, to obtain compounds according to the invention. The catalytic hydrogenolysis may be effected using hydrogen and a palladium oxide catalyst.

In order to convert compounds of formula (VI) where $R_7$ represents benzyl and compounds of formula (VII) in which $R_9$ represents hydrogen into compounds of the invention it is necessary to introduce a group R.

This may be effected by reductively alkylating the compounds of formula (VI) wherein $R_7$ represents a benzyl group and $R_8$ has the meaning given above with an appropriate ketone e.g. of formula (VIII).

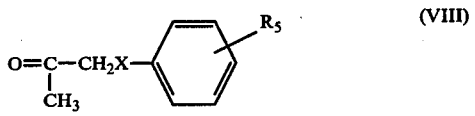

in the presence of hydrogen and a suitable catalyst such as platinum on charcoal or palladium on charcoal.

Alternatively one may take an amine of formula (IX)

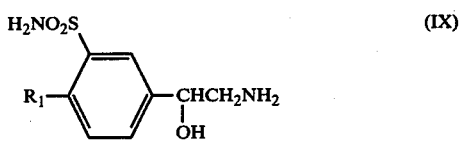

and condense it with an appropriate ketone yielding a group R, e.g. of formula (VIII), the product being subsequently reduced either by catalytic hydrogenation or by using a reducing agent such as sodium borohydride, to give a compound of formula according to the invention.

The reductive alkylation may also be carried out directly on a ketone of formula (X)

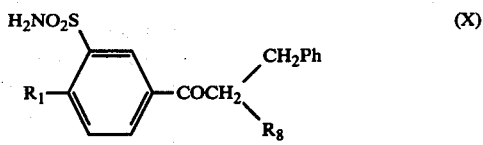

in which $R_8$ has the meaning given above to give compounds of formula according to the invention.

In an alternative process for the production of compounds according to the invention, a glyoxal of formula (XI)

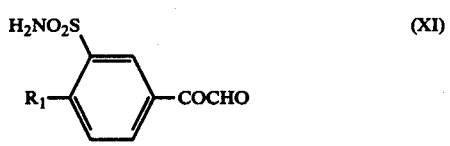

in which $R_1$ has the meaning given above, is used as the starting material. On condensation with an amine of formula (XII)

the glyoxal yields an intermediate azomethine of formula (XIII)

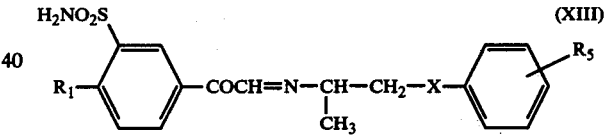

which is then reduced with, for example, a complex metal hydride, e.g. sodium borohydride, or hydrogen and a noble metal catalyst, to give a compound of formula (I).

In another method one may react a halohydrin of formula (XIV) or an epoxide of formula (XV).

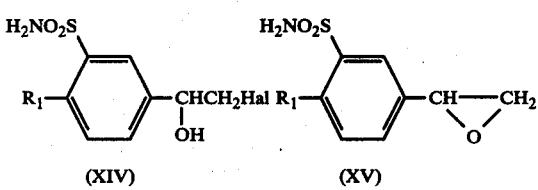

in which $R_1$ has the above stated meaning and Hal represents a halogen atom, with an amine of formula (XII). Where $R_1$ represents a halogen atom it is generally convenient for this to be present in the starting materials. Where $R_1$ is a group $NR_2R_3$, this may conveniently be introduced by treating compounds of formulae (II), and (X) in which $R_1$ is halogen, with ammonia or an amine $NHR_2R_3$ in a solvent, preferably ethanol. In the production of compounds of formula (I) where $R_2$ is H and R₃ is other than H, an amine HN(R₃)CH₂Ph may be used, with subsequent removal of the benzyl group.

The compounds according to the invention may be isolated as such or in the form of non-toxic physiologically acceptable salts.

The compounds according to the invention may be formulated for use in human or veterinary medicine for therapeutic or prophylactic purposes. The invention therefore includes within its scope, pharmaceutical compositions comprising as active ingredients, compounds of general formula (1) or physiologically acceptable addition salts thereof. As stated, preferred salts include the hydrochloride, maleate, tartrate etc. Such compositions may be presented for use in a conventional manner with the aid of carriers or excipients and formulatory agents as required, and with or without supplementary medicinal agents. These compositions include, for instance, solid or liquid preparations for oral use, suppositories and injections. Oral administration is most convenient in the form of tablets which may be prepared according to conventional methods and may be coated if desired. Injections may be formulated with the aid of physiologically acceptable carriers and agents as solutions, suspensions, or as dry products for reconstitution before used. The doses of the active ingredient which may be used may vary within a wide range. Suitable dosage units are generally within the range of 5 mg to 100mg, preferably 20mg to 200mg. A suitable daily dose would be within the range of 300 mg to 300mg orally, depending on the age and weight of the patient and the severity of the symptoms.

In order that the invention may be more fully understood, the following Examples are given, by way of illustration only.

EXAMPLE 1

2-Chloro-5-[1-hydroxy-2-[(1-methyl-3-phenylpropyl)amino]ethyl]-benzene-sulphonamide, hydrochloride a. 5-(2-Bromoacetyl)-2-chlorobenzenesulphonamide A solution of 5-acetyl-2-chlorobenzenesulphonamide (4.7 g) in glacial acetic acid (100 ml) was treated with bromine (3.2 g) in glacial acetic acid (20 ml), added dropwise with vigorous stirring at 50°. After an initial induction period of 5 minutes the colour of bromine was discharged. The addition took 30 minutes. The resulting solution was stirred for 15 minutes before removing the acetic acid under reduced pressure. The resulting white solid was dissolved in acetone (30 ml), diluted with benzene (250 ml) and the solution concentrated until the volume of solution was 150 ml. On cooling white crystals were deposited, 4.1 g, m.p. 168-172°.

b. 2-Chloro-5-[1-hydroxy-2-[N-(1-methyl-3-phenylpropyl)-N-(phenylmethyl)amino]ethyl]benzenesulphonamide A mixture of 5-(2-bromoacetyl)-2-chlorobenzenesulphonamide (3.13 g) in butanone (50 ml) and N-(1-methyl-3-phenylpropyl)-N-(phenylmethyl)amine (4.8 g) was heated under reflux for 30 minutes. The solvent was removed under reduced pressure and the residue triturated with dry ether and filtered. The ether solution was evaporated to dryness and the product dissolved in ethanol (50 ml) and treated with sodium borohydride (0.3 g). The mixture was stirred for 30 minutes and a further aliquot of sodium borohydride (0.3 g) was added. The reaction mixture was acidified with 2N hydrochloric acid and the ethanol removed under reduced pressure. The concentrate was bastified with 5N sodium hydroxide and the mixture extracted with ethyl acetate (2 × 50 ml). The extracts were washed with water (2 × 50 ml), dried (MgSO₄) and evaporated to dryness to give the product as a yellow oil, 4.6 g. This oil was purified by chromatography on preparative chromatographic plates (silica, CHCl₃/5% MeOH) and converted into a hydrochloride salt m.p. 120-125°.

c. 2-Chloro-5-[1-hydroxy-2-[(1-methyl-3-phenylpropyl)-amino]ethyl]benzenesulphonamide, hydrochloride A solution of 2-chloro-5-[1-hydroxy-2-[N-(1-methyl-3-phenylpropyl)-N-(phenylmethyl)amino]ethyl]-benzenesulphonamide (0.5 g) was hydrogenated over palladium oxide (0.05 g) for 18 hours (64 ml of hydrogen taken up; theory 48 ml). The catalyst was filtered off, washed with ethanol, and the resulting solution evaporated to dryness under reduced pressure to give the product as a white foam, 0.3 g, m.p. 88-94°.

EXAMPLE 2

2-Fluoro-5-[1-hydroxy-2-[[3-(4-fluorophenyl)-1-methylpropyl]-amino]ethyl]benzenesulphonamide, hydrochloride a. 5-(2-Bromoacetyl)-2-fluorobenzenesulphonamide A solution of 5-acetyl-2-fluorobenzenesulphonamide (1.0 g) in acetic acid (30 ml) was treated dropwise with a solution of bromine (0.736 g) in acetic acid (4.5 ml) at 50° in the presence of a few drops of 48% hydrogen bromide in acetic acid. After stirring for 15-20 minutes, the solvent was removed under reduced pressure. The residue was dissolved in ethyl acetate (50 ml) and washed with 8% sodium bicarbonate (50 ml) and water (50 ml). The organic layer was then dried (MgSO₄) and concentrated to give a pale brown oil which crystallised from benzene/acetone, 1.2 g, m.p. 129-132°.

b. 2-Fluoro-5-[[bis(phenylmethyl)amino]acetyl]benzenesulphonamide hydrochloride

Dibenzylamine (1.94 ml) in butanone (5 ml) was added dropwise to a stirred solution of 5-(bromoacetyl)-2-fluorobenzenesulphonamide (1.0 g) in butanone (60 ml). Stirring was continued for 3 hours at room temperature. The precipitated solid was filtered off and the filtrate concentrated under reduced pressure. The residue was converted into a hydrochloride salt, 1.01 g, m.p. 198°-200°.

c. 2-Fluoro-5-[1-hydroxy-2-[[-3-(4-fluorophenyl)-1-methyl propyl]amino]ethyl]benzenesulphonamide hydrochloride A mixture of 2-fluoro-5-[[bis(phenylmethyl)amino]acetyl]benzenesulphonamide (2.2 g) and 4-[4-fluorophenyl]-butan-2-one (3.48 g) in ethanol (50 ml) was hydrogenated at room temperature and pressure in the presence of prereduced 10% palladium oxide on carbon (0.42 g) and 5% platinum oxide on carbon (0.42 g) until uptake of hydrogen had ceased. The catalyst and solvent were removed and the residue dissolved in ethyl acetate and precipitated with petroleum ether (b.p. 60°-80°). The crude product was chromatographed on silica (Merck 70-230 mesh, 35 g) and eluted with ethyl acetate containing 10 drops of ammonium hydroxide per 250 ml. The first fraction (300 ml) was discarded but evaporation of the second fraction (375 ml) gave a colourless oil (0.8 g) which was converted into a hydrochloride salt, 0.85 g, m.p. 95°-105°.

In a similar manner 2-fluoro-5-[[bis(phenylmethyl)amino]acetyl]-benzenesulphonamide (2.5 g) and 4-phenyl-butan-2-one (5 g) were converted into 2-fluoro-5-[1-hydroxy-2-[(1-methyl-3-phenylpropyl)amino]ethyl]- benzenesulphonamide, hydrochloride, 0.4 g, m.p. 80°–95°.

EXAMPLE 3

2-Dimethylamino-5-[1-hydroxy-2-[(1-methyl-3-phenyl-propyl)amino]ethyl]-benzenesulphonamide, dihydrochloride a. 5-Acetyl-2-dimethylaminobenzenesulphonamide A mixture of 5-acetyl-2-chloro-benzenesulphonamide (0.5 g) in ethanol (10 ml) and dimethylamine in ethanol (33%, 5 ml) was heated in a closed vessel on a steam bath for 16 hours. The solvents were removed under reduced pressure and the residue crystallised from ethanol to give the product 0.31 g, m.p. 184°–185°.

b. 5-Bromoacetyl-2-dimethylaminobenzenesulphonamide

A solution of 5-acetyl-2-dimethylaminobenzenesulphonamide (1 g) in chloroform (70 ml) was treated dropwise with bromine (0.75 g) in chloroform (10 ml) and with hydrogen bromide in acetic acid (48%, 2 ml). The mixture was stirred for 3 hours and filtered. The product, a bright yellow solid (2.04 g), rapidly decolourised in sunlight. The compound was partitioned between ethyl acetate (100 ml) and sodium carbonate (100 ml) and the organic layer was separated, washed with water, dried (MgSO$_4$) and evaporated to dryness. The residue was recrystallized from ethyl acetate to give the bromo-acetyl compound 1.1 g, m.p. 142°–143°.

c. 2-Dimethylamino-5-[1-hydroxy-2-[bis(phenylmethyl)amino]ethyl]benzenesulphonamide hydrochloride A solution of 5-bromoacetyl-2-dimethylaminobenzenesulphonamide (2.4 g) in butanone (100 ml) was treated with dibenzylamine (1.5 ml) and propylene oxide (10 ml) and the mixture heated under reflux for 4.5 hours before removing the solvent under reduced pressure. The resulting yellow oil was dissolved in absolute ethanol and treated with sodium borohydride (1.2 g) for 1 hour before acidifying the mixture with dilute hydrochloric acid and removing the ethanol under reduced pressure. The product was extracted into ethyl acetate (3 × 150 ml), and the organic layer was washed with sodium bicarbonate solution (100 ml), water (100 ml), and then dried (MgSO$_4$) and evaporated to dryness. The residue was converted into a hydrochloride salt 1.5 g, m.p. 180°–183° (dec.).

d. 2-Dimethylamino-5-[1-hydroxy-2-[(1-methyl-3-phenylpropyl)amino]ethyl]benzenesulphonamide dihydrochloride A solution of 2-dimethylamino-5-[1-hydroxy-2-[bis(phenylmethyl)amino]ethyl]benzenesulphonamide (4.4 g) in absolute ethanol (300 ml) was hydrogenated over palladium on charcoal (0.5 g) and platinum on charcoal (0.5 g) with 4-phenylbutan-2-one at 50 p.s.i. and room temperature for 18 hours in a Cook hydrogenator. The catalyst was filtered off and the solvent removed under reduced pressure. The residual oil was dissolved in ethyl acetate (10 ml) and precipitated from petroleum ether (b.p. 60°–80°) (400 ml). The resulting oil was chromatographed on silica (Merck, 30 g) and eluted with ethyl acetate containing 10 drops 0.88 ammonia solution per 200 ml. The title compound was isolated as a foam and converted into the hydrochloride salt 2.6 g, m.p. 120°–130°.

In a similar manner 2-dimethylamino-5-[1-hydroxy-2-[bis(phenylmethyl)amino]ethyl]benzenesulphonamide (Compound A) was converted into the following compounds by reductive alkylation with the appropriate ketone.

2-Dimethylamino-5-[1-hydroxy-2-[(1-methyl-2-phenoxyethyl)amino]ethyl]benzenesulphonamide dihydrochloride, hydrate, (1.2 g) m.p. 120°–130° from Compound A (2.2 g) and 1-phenoxy-propan-2-one (2.7 g).

2-Dimethylamino-5-[1-hydroxy-2[[1-methyl-2-(methylphenyl)amino)ethyl]amino]benzenesulphonamide, trihydrochloride, (2.6 g) m.p. 130°–140° from Compound A (hydrochloride) (4.45 g) and 1-(methylphenylamino)-2-propanone (7.4 g)

2-Dimethylamino-5-[1-hydroxy-2-[(4-fluorophenyl)-1-methylpropyl]amino]ethyl]-benzenesulphonamide dihydrochloride, (2.0 g) m.p. 126°–134°, from Compound A (hydrochloride) (3.9 g) and 4-fluorobenzylacetone (6.6 g)

In this last case, hydrogenation took place for 65 hours rather than 18 hours.

EXAMPLE 4

5-[1-Hydroxy-2-[(1-methyl-3-phenylpropyl)amino]ethyl]-2-(1-piperidinyl)benzenesulphonamide, dihydrochloride, monohydrate a. 5-Acetyl-2-(1-piperidinyl)benzenesulphonamide A solution of 5-acetyl-2-fluorobenzenesulphonamide (1 g) and piperidine (0.98 g) in ethanol (50 ml) was heated under reflux for 3.5 hours. The solvent was removed and the residue was dissolved in ethyl acetate (100 ml) and washed with water (2 × 100 ml). The organic phase was dried (MgSO$_4$) and concentrated and the product was crystallised from isopropanol, 0.92 g, m.p. 130.5°–131.5°.

b. 5-(2-Bromoacetyl)-2-(1-piperidinyl)benzenesulphanamide, hydrobromide

A solution of bromine (1.13 g) in chloroform (23 ml) was added dropwise to a refluxing suspension of 5-acetyl-2-(1-piperidinyl)benzenesulphonamide (2 g) in chloroform (100 ml) and 48% hydrogen bromide in acetic acid (2.3 g). The suspension was then stirred for 1 hour and the chloroform decanted. The residue was recrystallised from ethanol/ethyl acetate to give the hydrobromide salt, m.p. 185°–189° (dec.).

c. 5-[1-Hydroxy-2-[bis(phenylmethyl)amino]ethyl]-2-(1-piperidinyl)benzenesulphonamide A solution of dibenzylamine (3.34 g) in butanone (10 ml) was added to a vigorously sitrred suspension of 5-(2-bromoacetyl)-2-(1-piperidinyl)benzenesulphonamide, hydrobromide (2.5 g) in butanone (100 ml). After 3 hours the mixture was filtered and the filtrate concentrated to a yellow oil. This oil was dissolved in ethanol (100 ml) and treated with sodium broohydride (0.42 g) at room temperature. After 1 hour, excess borohydride was destroyed with 2N hydrochloric acid. Ethanol was removed, the residue basified with 8% sodium bicarbonate solution and extracted with ethyl acetate (3 × 100 ml). The extracts were washed with water (100 ml), dried, and concentrated to a pale yellow oil (2.7 g). This was chromatographed on Merck Kieselgel 60 (50 g) to give the product as a white solid, 2 g, m.p. 133°–142°.

d. 5-[1-Hydroxy-2-[(1-methyl-3-phenylpropyl)amino]ethyl]-2-(1-piperidinyl)benzenesulphonamide; dihydrochloride, monohydrate A solution of 4-phenylbutan-2-one (1.73 g) and 5-[1-hydroxy-2-[bis(phenylmethyl)amino]ethyl]-2-(1-piperidinyl)benzenesulphonamide (1.4 g) in ethanol (200 ml) was hydrogenated over a mixture of 10% palladium on charcoal (0.28 g) and 5% palladium on charcoal (0.28 g) in a Cook hydrogenator at 40 p.s.i. during 24 hours. Catalyst and solvent were removed, and the residual oil dissolved in ethyl acetate (5 ml) and precipitated from petroleum ether (b.p. 60°–80°) (300 ml). This oil was chromatographed on silica (Merck) (30 g) and eluted with ethyl acetate containing 10 drops 0.88 ammonia solution per 200 ml. The title compound was isolated as a foam and converted into the hydrochloride salt, 800 mg, m.p. ill-defined but > 114°.

Found: C, 52.4; H, 6.7; N, 8.0; $C_{23}H_{33}N_3O_3S.2HCl.H_2O$ requires: C, 52.8; H, 7.1; N, 8.05%

EXAMPLE 5

2-Diethylamino-5-[1-hydroxy-2-[(1-methyl-3-phenylpropyl)amino]ethyl]benzenesulphonamide, dihydrochloride a. 5-Acetyl-2-diethylaminobenzenesulphonamide A solution of 5-acetyl-2-fluorobenzenesulphonamide (6.5 g), diethylamine (7.0 ml) and absolute ethanol (200 ml) was heated under reflux for 22 hours. The solution was concentrated to a gum under reduced pressure and partitioned between ethyl acetate (100 ml) and water (120 ml). The organic phase was separated and evaporated to dryness. Trituration of the residue with aqueous isopropanol gave the diethylamine compound as cream crystals, 5.9 g, m.p. 103°–105°.

b. 5-Bromoacetyl-2-diethylaminobenzenesulphonamide, hydrobromide

A stirred mixture of 5-acetyl-2-diethylaminobenzenesulphonamide (5.5 g), chloroform (275 ml) and 48% hydrogen bromide in acetic acid (13.75 ml) was treated with bormine (1.19 ml) in chloroform (110 ml) dropwise over a period of 2 hours. The reaction was then stirred at room temperature for 1 hour. The chloroform was decanted from the precipitated semi-solid which was washed with chloroform (300 ml) and then ethyl acetate (400 ml) to give the bromoketone, hydrobromide as a white crystalline solid (8.4 g) m.p. 135°–138° (from ethanol-ethyl acetate).

c. 2-Diethylamino-5-[1-hydroxy-2-(dibenzylamino)ethyl]-benzenesulphonamide

A solution of 5-bromoacetyl-2-diethylaminobenzenesulphonamide, hydrobromide (4.5 g), dibenzylamine (2.5 ml), propylene oxide (22.5 ml) and butanone (250 ml) was heated under reflux for 4 hours. The solvent was removed under reduced pressure and the residue dissolved in absolute ethanol (150 ml). Sodium borohydride (0.7 g) was added and the solution was stirred at room temperature overnight. The solution was evaporated to dryness under reduced pressure, acidified (2N hydrochloric acid) and then basified (sodium hydrogen carbonate) and extracted with ethyl acetate. The extracts were evaporated and the residue (6.2 g) was dissolved in ethanol and treated with ethereal hydrogen chloride and evaporated to dryness under reduced pressure. The solid obtained was triturated with ethyl acetate, to give the crude hydrochloride salt, 5.02 g, m.p. 230°–240° (from ethanol-ethyl acetate).

The salt (5.02 g) was dissolved in hot water, filtered and basified with sodium bicarbonate. The cooled solution was extracted with ethyl acetate (4 × 50 ml). Removal of the solvent gave the free base as a cream solid, 2.17 g, m.p. 133°–135°.

d. 2-Diethylamino-5-[1-hydroxy-2-[(1-methyl-3-phenylpropyl)amino]ethyl]benzenesulphonamide, dihydrochloride A mixture of 2-diethylamino-5-[1-hydroxy-2-(dibenzylamino)ethyl]benzenesulphonamide (1.17 g), 10% palladium oxide on carbon (0.2 g), 5% platinum oxide on carbon (0.2 g), 4-phenylbutan-2-one (1.48 g) and absolute ethanol (500 ml) was hydrogenated overnight at room temperature and 50 p.s.i. in a Cook hydrogenator. The catalyst and solvent were removed to give a mobile oil (2.0 g). This material was chromatographed on a column of silica (35 g, 70–230 mesh; Merck). Elution with ethyl acetate containing 0.88 ammonium hydroxide (10 drops of ammonium hydroxide per 250 ml of ethyl acetate) gave a first fraction of 200 ml which was discarded followed by a fraction of 270 ml which was concentrated under reduced pressure to leave a colourless oil (1.0 g). This oil was converted into a hydrochloride salt, 0.7 g, m.p. 140°–150°.

In a similar manner reductive alkylation of 2-diethylamino-5-[1-hydroxy-2-(dibenzylamino)ethyl]benzenesulphonamide, (Compound B) with the appropriate ketone gave the following compounds.

2-Diethylamino-5-[1-hydroxy-2-[[1-methyl-2-(methylphenylamino)ethyl]amino]ethyl]benzenesulphonamide, trihydrochloride (0.87 g) m.p. 140°–150° (dec.) from Compound B (2.25 g) and 1-(methylphenylamino)-2-propanone (3.25 g).

2-Diethylamino-5-[1-hydroxy-2-[[1-methyl-3-(4-fluorophenyl)propyl]amino]ethyl]benzenesulphonamide (0.5 g) m.p. 106°–110° from Compound B (1.9 g) and 4-fluorobenzylacetone (4.02 g). The catalyst in the latter two reactions was 10% palladium oxide on carbon only.

EXAMPLE 6

2-Amino-5-[1-hydroxy-2-[(1-methyl-3-phenylpropyl)amino]ethyl]benzenesulphonamide, dihydrochloride (a) 5-Acetyl-2-aminobenzenesulphonamide A solution of 5-acetyl-2-fluorobenzenesulphonamide (0.5 g) in ethanol (40 ml) saturated with ammonia was heated at 100° in a bomb overnight. Concentration of the resultant solution yielded a yellow crystalline solid, 0.4 g, m.p. 263°–264° (from ethanol).

b. 2-Amino-5-[2-bromoacetyl)benzenesulphonamide

A suspension of 2-amino-5-acetylbenzenesulphonamide (0.25 g) and cupric bromide (0.523 g) in ethyl acetate (15 ml) and chloroform (15 ml) was heated under reflux overnight. The cuprous bromide was filtered off and the filtrate was concentrated, dissolved in ethyl acetate (20 ml) and washed with water (2 × 20 ml). The organic phase was then dried and concentrated to give a colourless solid (0.3 g) which was shown by n.m.r. spectroscopy to be a 3:1 mixture of bromoketone and starting material. This was used without further purification.

c. 2-Amino-5-[1-hydroxy-2-[N-(1-methyl-3-phenylpropyl)-N-(phenylmethyl)amino]ethyl]benzenesulphonamide A solution of 2-amino-5-(2-bromoacetyl)benzenesulphonamide (0.5 g), N-(1-methyl-3-phenylpropyl)-N-(phenylmethyl) amine (0.45 g) and propylene oxide (2.5 ml) in 2-butanone (30 ml) was heated under reflux for 3 hours. The solution was then concentrated to a red-brown oil (0.7 g) which was dissolved in absolute ethanol (30 ml) and treated with sodium borohydride (258 mg) at room temperature during 2 hours. Excess borohydride was then destroyed with 2N hydrochloric acid and the ethanol was removed under reduced pressure. The residue was basified with 8% sodium bicarbonate and extracted with ethyl acetate (3 × 50 ml). The extracts were washed with water (100 ml), dried and concentrated to an orange oil (0.63 g). The oil was dissolved in acetone (10 ml) and re-precipitated as an orange solid (340 mg) by addition of petroleum ether (b.p. 60°–80°). Chromatographic purification of this solid on silica plates [Merck St17; elution with chloroform: methanol (5:1)] and conversion of the product into a hydrochloride salt gave the title compound, 0.2 g, m.p. 133°–136°.

d. 2-Amino-5-[1-hydroxy-2-[(1-methyl-3-phenylpropyl)amino]ethyl]benzenesulphonamide dihydrochloride A solution of 2-amino-5-[1-hydroxy-2-[N-(1-methyl-3-phenylpropyl)-N-(phenylmethyl)amino]ethyl]benzenesulphonamide (0.2 g) in ethyl acetate (50 ml) and acetic acid (ml) was hydrogenated over 10% palladium oxide on charcoal (200 g). Hydrogen uptake was 13.5 ml over 80 minutes (theoretical uptake 10.6 ml). The catalyst was filtered off and the filtrate diluted with dry ether (150 ml). The hydrochloride salt was precipitated by addition of ethereal hydrochloric acid, 130 mg, m.p. 129°–136° (dec.).

EXAMPLE 7

2-Ethylamino-5-[1-hydroxy-2-[(1-methyl-3-phenylpropyl)amino]ethyl]benzenesulphonamide, sesquihydrochloride a. 5-Acetyl-2-ethylamino-benzenesulphonamide A solution of 5-acetyl-2-fluorobenzenesulphonamide (6.0 g) and ethylamine (70% solution in water, 25 ml) in absolute ethanol (100 ml) was heated at 100° for 16 hours in a bomb. The resulting yellow solution was evaporated to small volume to deposit the title compound as an off-white crystalline solid, 6.0 g, m.p. 201°–204° (from ethanol).

b. 5-(Bromoacetyl)-2-ethylaminobenzenesulphonamide

A solution of 5-acetyl-2-ethylaminobenzenesulphonamide (2.4 g) in ethyl acetate (100 ml) and chloroform (100 ml) was heated under reflux with stirring for 18 hour in the presence of cupric bromide (4.4 g). The precipitate was filtered off and the solvent was removed under reduced pressure. The resulting brown solid was dissolved in ethyl acetate (200 ml) and washed with water (2 × 10 ml), dried and evaporated to dryness. The residue was recrystallised twice from chloroform to give the title compound as an off-white crystalline solid, 1.6 g, m.p. 156°–157°.

c. 2-Ethylamino-5-[1-hydroxy-2-(1-methyl-3-phenylpropyl)amino]ethyl]benzenesulphonamide, sesquihydrochloride A solution of 5-bromoacetyl-2-ethylaminobenzenesulphonamide (0.96 g) and N-(1-methyl-3-phenylpropyl)-N-(phenylmethyl)amine (1.4 g) and propylene oxide (5 ml) in butanone (70 ml) was heated under reflux for 4.5 hours. The solvent was removed under reduced pressure to give a pale yellow oil which was added dropwise to petroleum ether (b.p. 60°–80°) (200 ml) to give a gummy solid. This material, without further purification, was dissolved in ethyl acetate (100 ml) and hydrogenated over palladium on charcoal (0.3 g) and platinum on charcoal (0.3 g) in the presence of acetic acid (2 ml) for 18 hours. The catalyst was filtered off and the resulting colurless solution was treated with ethereal hydrogen chloride to give a hydrochloride salt, 1.0 g, m.p. 120°–125°.

EXAMPLE 8

5-[1-Hydroxy-2-[(1-methyl-3-phenylpropyl)amino]ethyl]-2-methylaminobenzenesulphonamide, dihydrochloride a. 5-Acetyl-2-[N-methyl-N-(phenylmethyl)amino]benzenesulphonamide A solution of 5-acetyl-2-chlorobenzenesulphonamide (0.7 g) and benzylmethylamine (1.1 g) in ethanol (40 ml) was heated in a bomb at 120° for 3 days. The resulting red solution was evaporaed to small volume to deposit the title compound as pale yellow crystals which were recrystallised twice from absolute ethanol to give an off-white crystalline solid, 0.4 g, m.p. 159°–161°.

b. 5-Bromoacetyl-2-methylaminobenzenesulphonamide

A solution of 5-acetyl-2-(N-methyl-N-phenylmethylamino)-benzenesulphonamide (0.96 g) in chloroform (40 ml) was added with stirring to a suspension of cupric bromide (1.4 g) in refluxing ether acetate (50 ml) over a period of 30 minutes and the resulting mixture stirred with refluxing for a further 16 hours. The precipitated cuprous bromide was filtered off and the solution evaporated to dryness. The resulting dark oil was dissolved in chloroform (50 ml), filtered through diatomaceous earth and evaporated to dryness to give a yellow foam (0.9 g). This material was recrystallized twice from chloroform to give the title compound, 0.6 g, m.p. 170°–172° (dec.).

c. 5-[1-Hydroxy-2-[(1-methyl-3-phenylpropyl)amino]ethyl]-2-methylaminobenzenesulphonamide, dihydrochloride A solution of 5-bromoacetyl-2-methylaminobenzenesulphonamide (1.0 g) and N-benzyl-2-amino-4-phenylbutane (1.2 g) in butanone (70 ml) was heated under reflux with propylene oxide (5 ml) for 4.5 hours. The solvent was removed under reduced pressure to give a pale yellow oil which was added dropwise to petroleum ether (b.p. 60°–80°, 100 ml) to give a gummy solid. This material, without further purificatiion, was dissolved in ethyl acetate (100 ml) and acetic acid (2 ml) and hydrogenated over palladium on charcoal (0.3 g) and platinum on charcoal (0.3 g) for 18 hours. Hydrogen uptake (200 ml) theoretical uptake (145 ml). The catalyst was filtered off and the resulting colourless solution treated with ethereal hydrogen chloride to precipitate a white solid which became pink after several minutes. This solid was filtered off and dried under vacuum to give the title compound as a brown solid, 1.0 g, m.p. 115°–125°.

EXAMPLE 9

2-Chloro-5-[2-[[3-(4-fluorophenyl)-1-methylpropyl]amino]-1-hydroxyethyl]benzenesulphonamide, hydrochloride, hydrate (a) 2-Chloro-5-[2-[[3-(4-fluorophenyl)-1-methylpropyl]phenylmethyl]amino]-1-hydroxyethyl]benzenesulphonamide, hydrochloride A solution of 5-bromoacetyl-2-chlorobenzenesulphonamide (2.0 g) in acetone (60 ml) was treated with N-[3-(4-fluorophenyl)-1-methylpropyl]-N-(phenylmethyl)amine (from 2.6g., 0.012 mol of hydrochloride) at about 20° C. for 16 hour. The acetone was then removed under reduced pressure and the residual oil triturated with dry ether. The solid hydrobromide was removed by filtration and the ether solution was evaporated to dryness. The residue was dissolved in ethanol (40 ml) and treated with sodium borohydride (1.0g, 4.0 equiv) and the mixture stirred at room temperature for 2 h before acidifying with 2N hydrochloric acid and removing the ethanol under reduced pressure. The pH was adjusted to 10 by the addition of 5N. sodium hydroxide and the mixture extracted with ethylacetate (3 × φml). The organic layer was washed with water (2 × 30 ml), dried (MgSO$_4$) and evaporated to dryness. The resulting oil was chromatographed on preparative silica plates and the major component was separated and treated with ethereal hydrogen chloride to give the title compound as a white solid 0.7g; m.p. 110–120°.

b. 2-Chloro-5-[2-[[3-(4-fluorophenyl)-1-methylpropyl]amino]-1-hydroxyethyl]benzenesulphonamide, hydrochloride, hydrate.

A solution of 2-chloro-5-[2-[[3-(4-fluorophenyl)-1-methylpropyl]phenylmethyl)amino]-1-hydroxyethyl]-benzenesulphonamide, hydrochloride (0.2 g). in absolute ethanol (30 ml) was hydrogenated over 10% palladium oxide on charcoal (20 mg.) until the rate of uptake of hydrogen had virtually ceased and 15 ml of hydrogen had been absorbed. The catalyst was filtered off and the filtrate was evaporated under reduced pressure to give the title compound 0.135 g. as a white friable solid.

Found: C, 47.5; H, 5.3; N, 5.9; $C_{18}H_{22}ClFN_2O_3S.HCl.H_2O$ requires: C, 47.4; H, 5.5; N, 6.1%

EXAMPLE 10

2-Dimethylamino-5-[2-[[3-(3-fluorophenyl)-1-methylpropyl]amino]-1-hydroxyethyl]-benzenesulphonmide, dihydrochloride.

A solution of 5-[2-[bis(phenylmethyl)amino]-1-hydroxyethyl]-2-[dimethylamino]-benzenesulphonamide (2.2g) in absolute ethanol (300 ml) was hydrogenated over palladium on charcoal (0.5 g.) and platinum on charcoal (0.5 g.) with 4-(3-fluorophenyl)-butan-2-one (3.3 g.) at 50 p.s.i. for 18 hours. The catalyst was filtered off and the solvent evaporated under reduced pressure to give a colourless oil which was filtered through a column of silica gel. The column was eluted with ethyl acetate/ammonia (10 drops per 250 ml of EtOAc) to give the product as a white foam. This was dissolved in ethyl acetate and treated with ethereal hydrogen chloride to give the title compound as an amorphous white solid. Yield 1.25 g., m.p. 115°–125°.

EXAMPLE 11

2-(Butylmethylamino)-5-[1-hydroxy-2-[(1-methyl-3-phenylpropyl)amino]ethyl]benzenesulphonamide, dihydrochloride.

A solution of 5-[[bis(phenylmethyl)amino]acetyl]-2-fluoro-benzenesulphonamide, hydrochloride (3g) and methylbutylamine (2.2 g) in ethanol (150 ml) was heated under reflux for 18 hr. The ethanol was removed and the residue was dissolved in ethyl acetate (150 ml), washed with sodium bicarbonate (8%, 200 ml) and water (200 ml) and dried MgSO$_4$). The solution was evaporated to a small volume and petroleum ether (b.p. 60°–80°, 520 ml) added. A red-brown gum (1.8 g) separated out. This was dissolved in ethanol (150 ml), added to a solution of 4-phenylbutan-2-one (4.9 g) in ethanol (150 ml) and hydrogenated over palladium oxide on charcoal (10%, 0.7 g) and platinum oxide on charcoal (5%, 0.7g) at 40 psi for 24 hr in the presence of acetic acid (2 ml). The catalyst and solvent were removed to give a mobile yellow oil (5g) which was chromatographed on a silica column (Merck Art, 7734, 75 g). After elution with ethyl acetate (500 ml) the product was isolated by elution with ethyl acetate: methanol (9:1) containing a trace of 0.88 ammonia to yield the product as a colourless foam (0.35 g). This material was dissolved in ethyl acetate (10 ml) and treated with ethereal hydrogen chloride (5 ml) to give the title compound, 0.4 g., m.p. 105°–110°.

EXAMPLE 12

2-Fluoro-5-[1-hydroxy-2-[[3-(3-fluorophenyl)-1-methylpropyl]amino]ethyl]benzenesulphonamide, hydrochooride, hemihydrate A solution of 5-[[bis(phenylmethyl)amino]acetyl]-2-fluorobenzenesulphonamide (2.4 g) and 4-(3-fluorophenyl)butan-2-one (2.9 g) in absolute ethanol (100 ml) was hydrogenated in the presence of prereduced 5% Pt/C (0.5 g) and 10% Pd/C (0.5g) until the reaction was judged to be complete by thin layer chromatography after 69 hr. The catalyst was filtered off and the filtrate was evaporated under reduced pressure to give a pale oil which was chromatographed on silica (Kieselgel 60, 70–230 mesh) (100 g). The column was eluted with ethyl acetate (1 liter) containing a trace of ammonia followed by 10% methanolethyl acetate (600 ml). The latter eluant was concentrated under reduced pressure to give an oil (1.2 g) which was triturated with ethyl acetate-petrol (b.p. 60°–80°) to give a pale viscous gum. This material was dissolved in ethyl acetate and treated with ethereal hydrogen chloride to give the title compound as a friable solid, 0.77 g., m.p. 65°–85°.

Found: C, 50.5; H, 5.7; N, 6.5; $C_{18}H_{22}F_2N_2O_3S.HCl\frac{1}{2}H_2O$ requires: C, 50.3; H, 5.4; N, 6.5%.

EXAMPLE 13

5-[1-Hydroxy-2-[(1-methyl-3-phenylpropyl)amino]ethyl]-2-(1-pyrrolidinyl) benzenesulphonamide, dihydrochloride, sesquihydrate.

a. 5-[2-[Bis(phenylmethyl)amino]-1-hydroxyethyl]-2-(1-pyrrolidinyl)benzenesulphonamide, dihydrochloride A mixture of 5-[[bis(phenylmethyl)amino]acetyl]-2-fluoro-benzenesulphonamide hydrochloride (0.5 g), pyrrolidine (0.2033 ml) and absolute ethanol (30 ml) was heated under reflux for 5 hr. A further aliquot of pyrrolidine (0.101 ml) was added and the solution heated at reflux for a further 2 hr.

The solution was allowed to cool and sodium borohydride (0.168 g) was added in one portion. After 2 hr the mixture was evaporated to dryness, acidified with hydrochloric acid and basified with sodium bicarbonate before extracting with ethyl acetate (4 × 40 ml). The combined extracts were washed with water (25 ml), dried (MgSO$_4$) and evaporated to dryness to give a cream foam (0.5 g). This material was chromatographed on Kieselgel 60 (70–230 mesh) and eluted with 1.1 cyclohexane/ethyl acetate (250 ml). Evaporation of the solvent gave the product as a pale cream foam (0.45 g) m.p. 45°–55°.

b. 5-[1-Hydroxy-2-[(1-methyl-3-phenylpropyl)amino]ethyl]-2-(1-pyrrolidinyl)benzenesulphonamide, dihydrochloride, sesquihydrate.

A solution of 5-[2-[bis(phenylmethyl)amino]-1-hydroxyethyl]-2-(1-pyrrolidinyl)benzenesulphonamide (3.5 g), 4-phenylbutan-2-one (4.43 g) and glacial acetic acid (1ml) in absolute ethanol (400 ml) was hydrogenated at 18°–20° and 50 p.s.i. in the presence of 10% palladium oxide on carbon (0.5 g) and 5% platinum oxide on carbon (0.5 g). The formation of the major product was monitored by thin layer chromatography and the reaction was considered complete after 118 hr.

The catalyst was filtered off and the filtrate concentrated under reduced pressure to give an oil which was triturated with ethyl acetate and petroleum ether (b.p. 60°-80°) to afford a light brown solid (2.7 g). This material was chromatographed on a silica column (Kieselgel 60, 70-230 mesh) (50 g) and eluted as follows:
1. Ethyl acetate (450 ml).
2. 10% Methanol/ethyl acetate + NH₄OH * (450 ml).
3. 10% Methanol/ethyl acetate + NH₄OH * (300 ml).

* (10 drops of 0.880 ammonium hydroxide per 250 ml of 10% methanol/ethyl acetate).

Evaporation of fraction 3 produced a cream foam (0.75 g) m.p. 50°-65°. This material was dissolved in ethyl acetate and treated with ethereal hydrogen chloride to give the title compound as a dihydrochloride salt 0.45 g., m.p. 140°-150°.

EXAMPLE 14

2-(Ethylmethylamino)-5-[1-hydroxy-2-[(1-methyl-3-phenylpropyl)amino]ethyl]benzenesulphonamide, dihydrochloride a. 5-[2-[Bis(phenylmethyl)amino]-1-hydroxyethyl]-2-(ethylmethylamino)benzenesulphonamide, dihydrochloride A mixture of 5-[[bis(phenylmethyl)amino]acetyl]-2-fluorobenzenesulphonamide hydrochloride (1.0 g), and ethylmethylamine (0.53 g) in absolute ethanol (100 ml) was heated in an autoclave at 100° overnight. The brown solution was allowed to cool and stirred with sodium borohydride (0.336 g) for 1 hr.

The mixture was evaporated to dryness, acidified (hydrochloric acid), basified (sodium bicarbonate) and extracted with ethyl acetate (4 × 50 ml). Evaporation of the dried solvent yielded a brown gum (1.3 g) which was chromatographed on Kieselgel 60 (70-230 mesh, 30 g) and eluted with 20% ethyl acetate/cyclohexane (500 ml). Evaporation of the solvent provided a cream foam (0.5 g) which was dissolved in ethyl acetate and treated with ethereal hydrogen chloride from ethanol/ethyl acetate to give the title compound as an off-white solid, 0.26 g, m.p. 188°-190° (from ethanol-ethyl acetate).

b. 2-(Ethylmethylamino)-5-[1-hydroxy-2-[(1-methyl-3-phenylpropyl)amino]ethyl]-benzenesulphonamide, dihydrochloride A mixture of 5-[2-[bis(phenylmethyl)amino]-1-hydroxyethyl]-2-(ethylmethylamino)-benzenesulphonamide (1.68 g), 4-phenylbutan-2-one) (2g) and glacial acetic acid (2ml) in absolute ethanol (400 ml) was hydrogenated in the presence of 10% palladium oxide/carbon (0.2 g) for 48 hr at 50 p.s.i. and 18°-20°.

The catalyst was filtered off and the filtrate evaporated under reduced pressure giving a pale brown oil (3.5 g). This material was partitioned between 8% aqueous sodium bicarbonate (25 ml) and ethyl acetate (25 ml). The ethyl acetate layer was separated, washed with water (10 ml), dried and evaporated under vacuum to give a pale brown oil (2.7 g). The crude product (1.3 g) was chromatographed on a silica (Kieselgel 60, 70-230 mesh) (26 g) and eluted as follows:
1. Ethyl acetate (75 ml)
2. 10methanol/ethyl acetate + NH₄OH * (125 ml)
3. 10% methanol/ethyl acetate + NH₄OH * (150 ml)

* 10 drops of 0.880 ammonium hydroxide per 250 ml of 10% methanol/ethyl acetate.

Evaporation of fraction (3) produced a cream foam (1.1 g). This material was dissolved in ethyl acetate and treated with ethereal hydrogen chloride to given the title compound as a yellow solid, 1.10 g, m.p. 130°-150°.

Analysis Found: C, 51.7; H, 7.1; N, 7.8; C₂₁H₃₁N₃O₃S.2HCl.⅓EtOAc.⅔H₂O requires: C, 51.6; H, 7.2; N, 8.1%

EXAMPLE 15

5-[1-Hydroxy-2-[(1-methyl-3-phenylpropyl)amino]ethyl]-2-(4-methylpiperazin-1-yl)benzenesulphonamide, trihydrochloride.

a. 5-[2-[Bis(phenylmethyl)amino]-1-hydroxyethyl]-2(4-methyl-piperazin-1-yl)-benzenesulphonamide A solution of 5-[[bis(phenylmethyl)amino]acetyl]-2-fluorobenzenesulphonamide, hydrochloride (4.48 g) in absolute ethanol (200 ml) containing N-methylpiperazine (4.485 g) was heated under reflux for 21 hr.

The solution was allowed to cool and stirred with sodium borohydride (1.52 g) for 2 hr at 18°-20°.

The resulting mixture was evaporated to dryness and acidified with hydrochloric acid. The solution was basified with aqueous sodium bicarbonate and extracted with ethyl acetate (4 33 50 ml). The organic phase was washed with water (25 ml), dried and concentrated under reduced pressure to give a gum (4.45 g). Reprecipitation from ethyl acetate with petroleum ether (b.p. 60°-80°) yielded a light cream solid, 3.9 g, m.p. 120°-130°.

b. 5-[1-Hydroxy-2-[(1-methyl-3-phenylpropyl)amino]ethyl]-2(4-methyl-piperazin-1-yl)benzenesulphonamide, trihydrochloride A solution of 5[2-[bis(phenylmethyl)amino]-1-hydroxyethyl]-2-(4-methyl-piperazin-1-yl)-benzenesulphonamide (3.5 g), 4-phenylbutan-2-one (4.22 g) and acetatic acid (1 ml) in absolute ethanol (400 ml) was hydrogenated at 50 p.s.i. and 18°-20° in the presence of 10% palladium oxide/carbon and 5% platinum oxide/carbon.

After 70 hr the catalysts were replaced and the hydrogenation was continued in the presence of a further quantity of 4-phenylbutan-2-one (4.22 g) and acetic acid (1 ml) for 18 hr.

The catalysts were filtered off and the filtrate was evaporated to dryness to give a brown oil. This material was triturated with ethylacetate - petroleum ether (b.p. 60°-80°) and the crude product (2.2 g) was chromatographed on Kieselgel 60 (70-230 mesh) (50 g) and eluted as follows:
1. Ethyl acetate
2. 10% methanol/ethyl acetate + NH₄OH *
3. 15% methanol/ethyl acetate + NH₄OH *

* (10 drops of 0.880 NH₄OH per 250 ml of eluant).

Evaporation of fraction (3) produced a colourless oil (0.73 g) which was dissolved in ethyl acetate and treated with ethereal hydrogen chloride to give the title compound as a trihydrochloride salt 0.58 g., m.p. 180°-190°.

PHARMACEUTICAL EXAMPLES

Examples of Pharmaceutical Compositions (a) Tablets:
(1) Prescription for preparing 10,000 tablets containing 20mg active ingredient.

Mix together 200g. active ingredient 795g. microcrystalline cellulose BPC and 5g. magnesium stearate BP. Compress the powders on a suitable tabletting press to produce tablets 6.5mm diameter and weighing approximately 100mg.

(2) Prescription for preparing 10,000 tablets containing 100mg active ingredient.

Mix together 1000g. active ingredient, 250g. lactose BP 172.5g. dried maize starch BP. Disperse 70g. pregelatinised maize starch BP in 1 liter cold water and moisten the powder mix with this to produce a damp cohesive mass. Pass the damp mass through a No. 14 mesh BSS sieve and dry the resultant granules at 60° C. Pass the dried granules through a No. 22 BSS sieve and mix with 7.5g. magnesium stearate. Compress the lubricated granules on a suitable tabletting press to produce tablets 8mm in diameter weighing about 150mg. The tablets may be film coated with a suitable film forming material such as methyl cellulose or hydroxy propylmethyl cellulose using standard techniques. The tablets may also be sugar coated.

(b) Capsules:

Prescription for preparing 10,000 capsules each containing 50mg active ingredient.

Mix together 500 g. active ingredient with 700 g. microcrystalline cellulose BPC and fill into No. 3 hard gelatin capsules so that each capsule contains approximately 120 mg of the mixture.

(c) Injection:

Prescription for preparing an injection containing 10mg active ingredient per ml.

Dissolve 10g active ingredient and 7.5g sodium chloride BP. in 950ml water for injections. When solution is complete, make up to 1 liter with more water for injections. Subdivide the solution into suitable sized ampoules (1, 5 or 10ml) seal and sterilise by heating in an autoclave. The active ingredient in the compositions may be any compound according to the invention.

We claim:

1. Compounds of the general formula

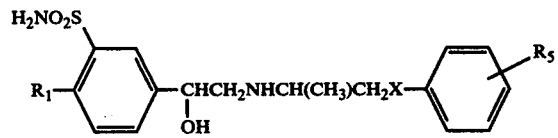

or physiologically acceptable salts thereof, in which $R_1$ is a halogen atom or a group $NR_2R_3$;

$R_2$ and $R_3$, which may be the same or different, are hydrogen or ($C_1$-$C_6$) straight or branched chain alkyl; or $R_2$ may be hydrogen and $R_3$ may be group $R_4CO$ or $R_4SO_2$ where $R_4$ is hydrogen or alkyl ($C_{1-4}$);

$R_5$ is hydrogen or one or more halogen atoms or hydroxy or alkoxy ($C_{1-4}$) groups; and X is $CH_2$, O or a group $NR_6$ where $R_6$ is hydrogen or alkyl ($C_{1-4}$).

2. Compounds as claimed in claim 1 in which $R_1$ is chlorine, fluorine, amino, alkyl ($C_{1-4}$) amino, or dialkyl ($C_{1-4}$) amino.

3. Compounds as claimed in claim 1 in which $R_5$ is hydrogen or halogen.

4. Compounds as claimed in claim 3 in which $R_5$ is para-fluoro.

5. Compounds as claimed in claim 1 in which X is —$CH_2$—.

6. A compound as claimed in claim 1 which is 2-fluoro-5-[1-hydroxy-2[[3-(4-fluorophenyl)-1-methylpropyl]-amino]ethyl]benzenesulphonamide.

7. A compound as claimed in claim 1 which is 2-fluoro-5-[1-hydroxy-2-[(1-methyl-3-phenylpropyl)amino]ethyl]benzenesulphonamide.

8. A compound as claimed in claim 1 which is 2-dimethylamino-5-[1-hydroxy-2-[(1-methyl-3-phenylpropyl)amino]ethyl]benzenesulphonamide.

9. A compound as claimed in claim 1 which is 2-amino-5-[1-hydroxy-2-[(1-methyl-3-phenylpropyl)amino]ethyl]benzenesulphonamide.

10. A compound as claimed in claim 1 which is 5-[1-hydroxy-2-[(1-methyl-3-phenylpropyl)amino]ethyl]-2-methylaminobenzenesulphonamide.

11. A compound as claimed in claim 1 which is 2-(butylmethylamino)-5-[1-hydroxy-2-[(1-methyl-3-phenylpropyl)amino]ethyl]benzenesulphonamide.

12. A compound as claimed in claim 1 which is 2-fluoro-5-[1-hydroxy-2-[[3-(3-fluorophenyl)-1-methylpropyl]amino]ethyl]benzenesulphonamide.

13. A compound as claimed in claim 1 which is 2-(ethylmethylamino)-5-[1-hydroxy-2-[(1-methyl-3-phenylpropyl)amino]amino]ethyl]benzenesulphonamide.

14. A process for the preparation of compounds as claimed in claim 1 which comprises;

a. reducing compounds of the general formula:

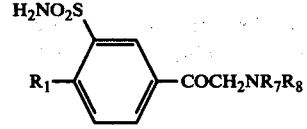

in which $R_1$ has the meaning given in claim 1 and $R_7$ represents a group R of the formula:

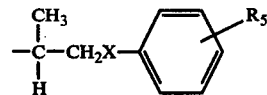

in which X and $R_5$ have the meanings given in claim 1 and $R_8$ represents hydrogen or benzyl, with subsequent conversion of the group $R_8$ when this is benzyl to hydrogen; or b. reductively alkylating a compound of the formula:

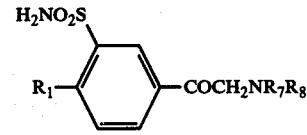

or the corresponding alcohol thereof in which $R_1$ has the meaning given in claim 1, and $R_7$ represents benzyl and $R_8$ represents hydrogen or benzyl with a ketone of the formula:

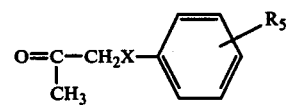

in which $R_5$ and X have the meaning given in claim 1; or
c. condensing an amine of the formula:

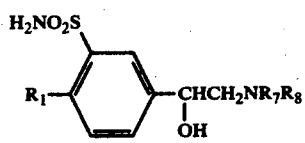

in which $R_1$ has the meaning given in claim 1 and $R_7$ and $R_8$ are both hydrogen, with a ketone of the formula

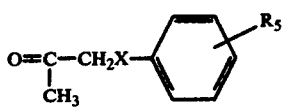

in which $R_5$ and X have the meanings given in claim 1 and reducing the resulting condensation product;
d. condensing a glyoxal of the formula

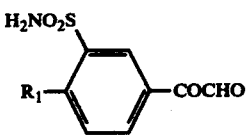

in which $R_1$ has the meaning given in claim 1, with an amine of the formula $RNH_2$, in which R has the meaning given in (a) above to provide an intermediate azomethine of the formula:

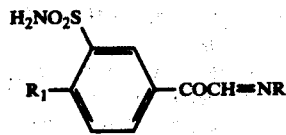

which is then reduced; or
e. reacting a halohydrin of the formula (XIV) or an epoxide of formula (XV):

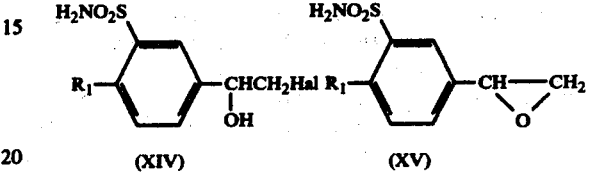

in which $R_1$ has the meaning given in claim 1 and Hal represents halogen, with an amine of the formula $RNH_2$ in which R has the meaning given in (a) above; the desired product in all cases being isolated in the free base or in the form of a physiologically acceptable salt thereof.

15. A process as claimed in claim 14(a) in which reduction is effected by a non-catalytic reduction procedure and subsequent debenzylation is effected by catalytic hydrogenolysis.